United States Patent [19]

Hamilton

[11] Patent Number: 5,254,526

[45] Date of Patent: * Oct. 19, 1993

[54] METHOD TO PREVENT ALGAE GROWTH IN POOLS AND SPAS

[76] Inventor: Jock Hamilton, 3741 E. Telegraph Rd., Piru, Calif. 93040

[*] Notice: The portion of the term of this patent subsequent to Jul. 11, 2006 has been disclaimed.

[21] Appl. No.: 397,973

[22] Filed: Aug. 24, 1989

[51] Int. Cl.$^5$ .................. A01N 59/08; A01N 59/26
[52] U.S. Cl. .................................. 504/119; 504/124
[58] Field of Search ............... 71/67; 210/753, 764

[56] References Cited

U.S. PATENT DOCUMENTS

| | | | |
|---|---|---|---|
| 2,662,855 | 9/1950 | Kamlet | 71/67 |
| 3,201,311 | 8/1965 | Antonides et al. | 71/67 |
| 3,316,173 | 4/1967 | Mills et al. | 71/67 |
| 3,975,271 | 8/1976 | Saunier et al. | 210/753 |
| 4,846,979 | 7/1989 | Hamilton | 210/754 |

FOREIGN PATENT DOCUMENTS 2095111A 9/1982 United Kingdom ............... 71/67

Primary Examiner—Glennon H. Hollrah
Assistant Examiner—B. Bembenick
Attorney, Agent, or Firm—R. Joseph Trojan

[57] ABSTRACT

The invention discloses an anti-microbial composition, and method for its use for the long term inhibition of the growth of algae in swimming pools, spas, and similar bodies of water. The method includes the addition of bromide ions to the body of water in amounts sufficient to provide a concentration of bromine of approximately 0.1 to 100 ppm. A polyphosphate is premixed with the source of bromide ions in a ratio of from 5 to 15 weight parts polyphosphate to each 100 weight parts of said source of bromide ions. A chlorine containing oxidizer is added to the water in a amount sufficient to oxidize the bromide ions to bromine and provide a concentration of chlorine containing oxidizer of approximately 0.2 to 10 ppm to safely sterilize the water.

8 Claims, No Drawings

METHOD TO PREVENT ALGAE GROWTH IN POOLS AND SPAS

BACKGROUND OF THE INVENTION

1. Field Of The Invention

This invention relates to a method to prevent the growth of algae in swimming pools and spas and to prevent and remove yellow algae stains from surfaces of the pools and spas.

2. Brief Statement Of The Prior Art

Many oxidizing agents have been used with limited success to prevent the growth of algae in swimming pools and spas; and to prevent the formation of yellow algae deposits on the surfaces of the pools and spas.

Examples of agents which have been used are: chlorine, salts and compounds of metals such as silver and copper, quaternary salts, polyquaternary salts, simazines and others. Unfortunately, the microorganisms, after an exposure period of 1 to 3 years, have adapted to these agents, and algae have been reported growing in waters containing 20 ppm chlorine, which is approximately 10 to 15 times the normal dosage level of chlorine in pool and spa waters.

I have discovered that bromine is a very effective algicide in pools and spas. My early work revealed that bromine was effective at dosages as low as 0.1 ppm. I discovered that bromine could be generated in a pool by the addition of a bromide salt, such as sodium bromide, to the pool, provided that the concentration of chlorine or hypochlorite was maintained in the pool during the treatment. In all my early test work, I used a soluble bromide in combination with a polyphosphate as an algicide and have found the combination effective in pools for periods of several years, without any signs that the algae can adapt to the bromine or acquire a tolerance for this agent. My use with the bromide and polyphosphate algicide, however, revealed concentration limits to the polyphosphate coadditive. In my initial work, I used mixtures which contained 25 percent of tetrasodium polyphosphate. This mixture caused clouding of the water when used on a regular maintenance program, in which the composition was added as needed to maintain the bromine content in the effective range. In ny initial work, the composition was also added at a large excess, however, it was found that this caused depletion of chlorine from the pool water, and the present method comprises the frequent addition of limited dosages of the composition to the water.

Bromine has been used as a sanitizer for pools and spas, but not as an algicide. Chloro bromo hydantoin (chloro bromo glycol urea) and a limited amount of a chlorine or hypochlorite releasing agent have been used as a two part additive system, as a sanitizer substitute for chlorine. Also sodium bromide and an oxidant such as oxypersulfate has recently been used as a sanitizer. Elemental bromine has also been used as a sanitizer in combination with a copper sulfate algicide. No mention or claim to the activity of bromine as an algicide has been made by the manufacturers of these products. Indeed, the bromine from these products is not active against algae, as it has not been employed in water which also contains chlorine or hypochlorite.

I have now found that a bromide, added alone to water which contains available chlorine, as chlorine, or as hypochlorite, or other chlorine oxidizers such as trichloro triazine trione, or sodium or potassium dichloro triazine trione, is an effective algicide. I have further found that in some applications, it may not be necessary or even desirable to add a polyphosphate. Accordingly, this invention comprises the use of a bromide salt together with a chlorine-containing oxidizer, as an algicide in a pool or spa, without the concurrent addition of a polyphosphate to the water.

DESCRIPTION OF PREFERRED EMBODIMENTS

The method of this invention comprises the addition of a water soluble bromide to swimming pools and spas, which contain an oxidizing agent such as chlorine. In a preferred form of the invention, the bromide is added as an algicide which comprises a mixture of two active agents which are a water soluble bromide, such as an alkali metal, alkaline earth metal or ammonium bromide, and a water soluble polyphosphate, such as an alkali metal or ammonium polyphosphate. The most preferred method is the subject of the claims of my aforementioned patent.

The alkali metal bromide salts, particularly potassium and sodium are preferred, and of the alkali metal salts, sodium is most preferred for its availability and low cost. Ammonium salts are operable and can be used when their cost and odor problems are not objectionable.

The bromide is an effective source of active bromine when contacted with a water soluble oxidizing agent having sufficient oxidation potential to oxidize bromide ions in dilute solutions, i.e., an oxidation potential more negative than $-1.1$ volts in dilute aqueous solutions, with respect to a standard hydrogen electrode. Examples of suitable oxidizing agents which are maintained in the water by the method of the invention comprise: chlorine, soluble hypochlorites, Oxone a commercial product of E. I. duPont de Nemoures & Company, soluble persulfates such as sodium or potassium persulfate, monoperoxyphthlate hexahydrate, etc. The selected oxidizer is maintained in the treated water at a concentration from 1 to about 200 ppm, sufficient to effect the oxidation of the bromide additive.

As previously mentioned, a water soluble polyphosphate can be included in the algicide composition at a concentration from 5 to about 15 parts for each 100 parts of bromide, and this is the most preferred composition. The polyphosphate functions as a non-foaming surfactant, and as an inhibitor on the surfaces of the pool or spa. When used in pools or spas with surfaces which have been stained by yellow algae deposits, the polyphosphate in the algicide composition is effective to remove the scale deposits. It is also believed that the polyphosphate serves to enhance the activity of the bromine containing algicide, and it was surprising to discover that the bromine containing additive is active in chlorine-containing waters without the presence of the polyphosphate.

In the method of the invention, the bromide composition and the chlorine-containing oxidizer are maintained in the water at concentrations which are effective to maintain the bromine in the water at a concentration from 0.5 to about 100 ppm. When the algicide is used in swimming pools and spas, the bromide algicide composition and oxidizer are maintained at concentrations which are effective to maintain bromine in the water at a concentration from 0.5 to about 50 ppm. Higher concentrations of bromine are not preferred as the bromine at levels above 50 ppm tend to impart a green color to the water. While higher concentrations of bromine can be used if color is not objectionable, e.g., for industrial uses such as cooling tower water, concentrations above about 100 ppm are not practical as no significant improvement in activity is achieved by using higher concentrations of bromine. The amount of the bromide compound which is added to the water depends somewhat on the use and prior treatments of the water. In most applications the bromide composition can be added in excess to the water, and the amount of the oxidizer which can be periodically added to the water can be limited to control the amount of bromine in the water to the aforementioned concentrations—from 12 to about 100, preferably from 5 to about 20, ppm. The oxidizer such as sodium hypochlorite can be added to the water in periodic intervals, e.g., once every 12 to 72 hours, preferably once every 36 to 56 hours. The amount of bromide composition which is initially added can be sufficient to provide bromine release over a period from about 5 to 30 days, preferably from 7 to about 14 days.

If desired, the algicide composition and the oxidizer can both be added continuously or at frequent intervals to maintain a relatively constant concentration of both of these additives.

The algicide composition can be added continuously, e.g., it can be slowly dissolving tablets which are placed in the water. Alternatively, the algicide composition can be added at intervals which are selected based on the severity of the algae growths and the use of the pool or spa.

Swimming pools and spas are typically treated with a chlorine-containing oxidizer, such as chlorine or a soluble hypochlorite or trichloro triazine trione, or sodium or potassium dichloro triazine trione. These oxidizers are often added to maintain a chlorine concentration in the pool. The chlorine concentration can be maintained at a level from 0.2 to about 10 ppm, preferably from 0.5 to about 2 ppm. In such applications, the bromide salt can be added with the chlorine oxidizer to the water in the aforementioned intervals and dosages.

Alternatively, the water in most pools and spas contains chlorine or a hypochlorite at the aforementioned concentrations, usually from about 0.5 to about 5 ppm, expressed as chlorine, as a general purpose algicide. In such applications, the algicide composition (bromide salt) could be added to the water at intervals of 12 hours to sixty days, or more preferably 168 hours to 30 days, and in amounts to provide from 5 to about 15 ppm of the water soluble bromide in the water with each addition.

In still other applications, the oxidation of the bromide can be effected electrolytically. In such applications, a water soluble bromide salt and a water soluble chloride salt can be added to the water and the water can be passed through an electrolytic cell to oxidize the dissolved salts to bromine and chlorine, and thereby provide the above-indicated concentrations of these active agents.

The invention will now be described with reference to the following examples which will also serve to demonstrate the results obtained when practicing the invention.

EXAMPLE 1

A swimming pool which is stained with yellow algae deposits is treated with the algicide composition of the invention which is disclosed and claimed in my prior patent. The history of the pool reveals that chlorine has been maintained in the pool at a level of about 1 ppm, and the chlorine is continued to be maintained at this level throughout the test period with the algicide composition. Despite this concentration of chlorine in the past, the algae have adapted and grown to the level where objectionable yellow stains have formed, particularly about the shady wall of the pool. The following algicide composition is added to the swimming pool water:

TABLE 1

| Ingredient | Concentration |
| --- | --- |
| Sodium Bromide | 90% (by weight) |
| Tetrasodium Pyrophosphate | 10% |

The algicide composition is added to the swimming pool water on a continuous basis at an amount of 3 full caps of its container (1 pound) at 47 hour intervals (every other day) and the chlorine is maintained in the swimming pool by the addition of 2 gallons liquid chlorine at the same time as the addition of the algicide composition.

The swimming pool is inspected on a regular basis and it is observed that the yellow stains began to disappear after the second day of treatment. After twenty days of treatment, the yellow stains have been completely removed from the pool.

The aforementioned procedure is followed with the following algicide composition:

TABLE 2

| Ingredient | Concentration |
| --- | --- |
| Sodium Bromide | 75% (by weight) |
| Tetrasodium Pyrophosphate | 25% |

It is observed that the water in the swimming pool becomes quite cloudy after the tenth day of treatment. When the addition of the algicide composition is discontinued, the water again becomes clear, however, after about four weeks, yellow algae stains again form on the surfaces of the pool.

When the addition of the algicide composition of Table 2 and the chlorine are added to the swimming pool water over a period slightly in excess of one year, the algae deposits do not reappear. Similar results, over a several month period, are observed using the treatment with the algicide composition of Table 1.

EXAMPLE 2

In another experiment, a swimming pool having a capacity of 10,000 gallons of water, and a history of algae growth in which many treatments had been attempted without success. The pool is treated by the addition of 3 pounds of the algicide composition of Table 1. An oxidizer, Trichloror S Triazine Trione, commercially available from Monsanto Chemical Company, is added to the water at a dosage of one pound twice a week, at regular intervals. The algicide composition is active and the bromine concentration is thereby maintained in the water at a value from 0.5 to about 1 ppm throughout a six week period. At the end of the sixth week, the addition of the chlorine oxidizer is continued, using slowly dissolving tablets. The pool remains free of algae growth and no yellow stains are observed throughout an extended test period of over two years.

EXAMPLE 3

The procedure of Example 2 is repeated with the composition of Table 2, however, liquid sodium hypochlorite is added to the pool rather than Trichloro S Triazine Trione. The liquid sodium hypochlorite (aqueous concentration of about 10–14 weight percent) is added to the pool at regularly spaced intervals twice a week, and the algicide composition is added in amounts of two pounds every six weeks. The pool remains free of algae growth throughout the test period.

EXAMPLE 4

The following examples will illustrate the discovery that the bromide agent, alone, is active against the algae, when present with an oxidizer of sufficient potential to oxidize the bromide to bromine.

Sodium bromide was added to 75 gallons of tap water and the water was stored for a sufficient period of time for the growth of green and yellow algae. After an observable quantity of algae appeared, chlorine was added to provide a chlorine content of 3 ppm chlorine in the water. The growth of algae was immediately arrested, the water partially cleared, and no further growth of algae occurred.

EXAMPLE 5

A sample (75 gallons) of tap water was stored without addition of any chemicals until yellow and green algae was observed growing in the water. Sufficient sodium bromide and sufficient chlorine were added to provide 1 ppm of each in the water. On the following day the water was inspected and it was observed that the growth of algae had been arrested, as evidenced by clearing of the water and the absence of further growths of algae.

EXAMPLE 6

A sample of tap water (75 gallons) was treated with chlorine to provide a concentration of chlorine of 2 ppm in the water. The water was stored until a bloom of green and yellow algae occurred. At that time, sodium bromide was added and the growth of algae was immediately arrested. The water was stored for an extended period, while maintaining its chlorine content at 0.2 ppm and the water remained free of further algae growth.

EXAMPLE 7

A sample of tap water (75 gallons) was treated with sodium bromide and a non-chlorine oxidizer (hydrogen peroxide) sufficient to provide hypobromous acid in the water. No chlorine was present. Upon storage for an extended period, yellow green algae was observed to have formed in the water. When chlorine was added to the water, the algae growth stopped immediately.

The experiment was repeated and Oxone (a commercial oxidizer which converts dissolved chlorides in the tap water to chlorine) was added when growth of algae was detected, and it was observed that the algae growth was immediately arrested.

The invention has been described as used as the sole algicide additive. It is equally useful in combination with other algicides and chlorine enhancers, such as sources of ammonia, e.g., ammonium sulfate, ammonium chloride, etc., quaternary ammonium compounds, metal algicides, e.g., copper salts; polyquats; etc. In such combinations, the invention is used in the manner described herein, and the supplemental algicide or chlorine enchancer can be added in the dosages recommended by the manufacturer or supplier of the particular additive. An advantage of the invention is that it is compatible with other water treatments, and under some circumstances, it may desirably be combined with such other treatments.

The invention has been described with reference to the illustrated and presently preferred embodiment. It is not intended that the invention be unduly limited by this disclosure of the presently preferred embodiment. Instead, it is intended that the invention be defined, by the means, and their obvious equivalents, set forth in the following claims:

What is claimed is:

1. A method of inhibiting the growth of algae in a body of water comprising:
   directly adding to said body of water a water soluble source of bromide ions in an amount sufficient to provide a concentration of bromine to approximately 0.1 ppm to 100 ppm, adding directly to said body of water a chlorine-containing oxidizer in amount sufficient to oxidize said source of bromide ions to bromide at the concentration specified and provide a concentration of chlorine containing oxidizer of approximately 0.2 ppm to 10 ppm sufficient to safely sterilize said body of water;
   said chlorine-containing oxidizer selected from the group consisting of chlorine, an alkali metal hypoclorite or trichlorotriazine trione, or sodium or potassium dichlorotriazine trione;
   adding an alkali metal, alkaline earth metal, or ammonium polyphosphate in proportions from approximately 5 to 15 weight parts of said polyphosphate per each 100 weight parts of said source of bromide ions; said polyphosphate being premixed with said source of bromide ions prior to addition to said body of water.

2. The method according to claim 1 wherein said source of bromide ions is added to the water in quantities from approximately 1 to 5 ounces.

3. The method according to claim 1 wherein, said source of bromide ions and said chlorine-containing oxidizer are added at intervals between approximately 12 to 72 hours in amounts sufficient to maintain the oxidized bromide in the water in the concentration specified.

4. The method according to claim 1 including, adding a greater amount of said source of bromide ions than can be oxidized by said added chlorine containing oxidizer; periodically adding additional chlorine-containing oxidizer to maintain the concentration of bromine at the level specified.

5. The method according to claim 1 wherein the body of water is a body of water in a swimming pool or spa and said oxidized bromide incorporated in said body of water acts as an algicide to prevent the growth of yellow algae and stains in said body of water.

6. The method of claim 5 wherein said body of water contains algae and said oxidized bromide is added in sufficient amounts to eradicate said algae from said swimming pool or spa.

7. The method of claim 1 comprising the step of adding a bromide source selected from the group consisting of alkali metal, alkaline earth metal or ammonium bromides or chloro bromo hydantoin.

8. The method of claim 7 wherein said bromide source is added to the water in an amount from 1 ounce to 3 pounds per 10,000 gallons of water.

* * * * *